Figure 1:
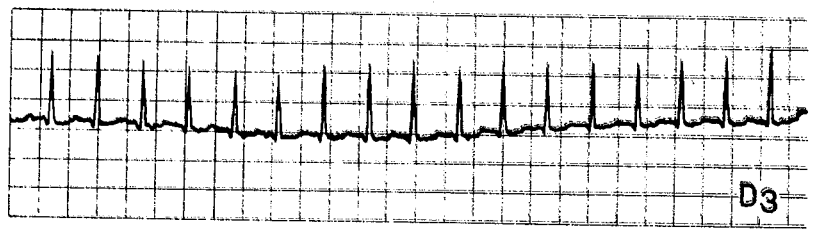

United States Patent [19]

Casagrande et al.

[11] 4,000,125
[45] Dec. 28, 1976

[54] NOVEL CARDIOTONIC STEROIDS, PROCESS FOR THEIR PREPARATION AND THERAPEUTICAL USE

[75] Inventors: Cesare Casagrande, Como; Giorgio Ferrari, Milan, both of Italy

[73] Assignee: Siphar S.A., Lugano, Switzerland

[22] Filed: July 30, 1975

[21] Appl. No.: 600,485

[30] Foreign Application Priority Data

Aug. 8, 1974  Switzerland ............ 10855/74

[52] U.S. Cl. ................... 536/7; 260/239.57; 260/239.55 R; 260/239.5
[51] Int. Cl.[2] ........................... C07J 1/00
[58] Field of Search ......... 260/210.5; 260/239.5; /Machine searched steroids

[56] References Cited

UNITED STATES PATENTS 3,838,163  9/1974  Saucy et al. ............ 260/239.5

*Primary Examiner*—Elbert L. Roberts
*Attorney, Agent, or Firm*—Cushman, Darby & Cushman

[57] ABSTRACT

The invention relates to novel steroid compounds having the formula

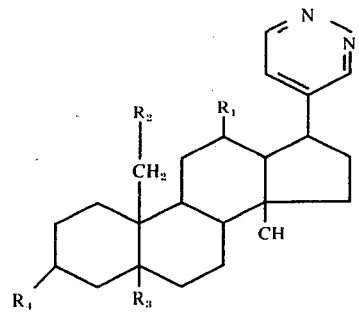

and their glycoside derivatives containing a pyridazine ring, in which particularly the substituent $R_4$ is a hydroxy group or a hexopyranoside unit or a chain of two or three hexopyranoside units, as it is normally found in the molecule of the natural glycosides; one or even all the hydroxy groups contained in the $R_4$ can be either free or etherified or esterified with either a simple carboxylic acid or a carboxylic acid bearing basic groups, or even acetalized with an aldehyde or a ketone, depending on the position and the orientation of a pair of hydroxy groups. The subject compounds are endowed with cardiotonic activity. The invention moreover relates to the process for the preparation of the above compounds and to their therapeutic use.

18 Claims, 2 Drawing Figures

NOVEL CARDIOTONIC STEROIDS, PROCESS FOR THEIR PREPARATION AND THERAPEUTICAL USE

The present invention relates to a group of novel cardiotonic steroids containing a pyridazine ring and the corresponding glycosides containing one or more carbohydrate molecules bonded at the 3 position of the steroidic system, as well as the derivatives of the afore mentioned compounds in which one or more hydroxyl groups are bonded, in form of ester or of acetals, to the preparation of these compounds and to their use.

The compounds of the invention correspond to the following formula (1):

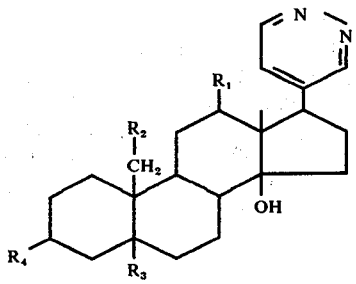

wherein $R_1$ and $R_2$ are hydrogen or a hydroxy group, either free or esterified with a carboxylic aliphatic acid, such as the formic, acetic, propionic and butyric acids, and preferably the acetic acid, $R_3$ is a hydrogen atom or a hydroxy group, and $R_4$ represents a hydroxy group, free or esterified with a carboxylic aliphatic acid, simple or even bearing basic groups, such as dimethylamino, diethylamino, piperidino, morpholino groups, such as the formic, acetic, propionic and butyric acids, preferably the acetic acid, or a hexopyranoside unit or a chain comprising two or three hexopyranoside units, as they are normally encountered in the molecules of the natural glycosides (see, for instance, L. Fieser and M. Fieser, Steroids, Reinhold Publishing Corp., New York, 1959, pag. 729–733); thus, for example, in the case of a monoside, the hexapyranoside unit can be a molecule of α-L-rhamnose, in which case $R_4$ is representing:

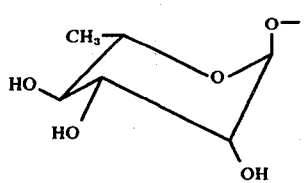

or a molecule of α-L-thevetose, in which case $R_4$ is representing:

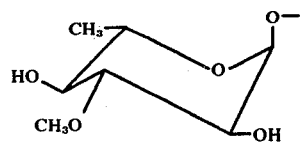

As a further example, in the case of a trioside, the chain of three hexapyranoside units can be formed by three molecules of β-D-digitoxose and in this case $R_4$ represents:

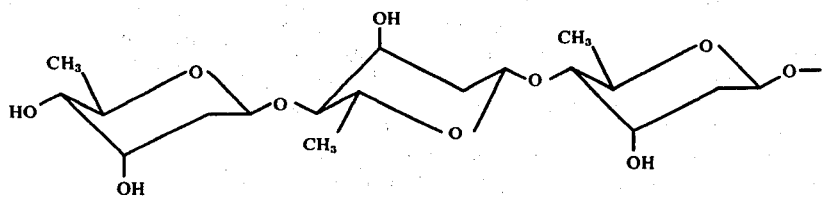

Some or all the hydroxy groups of the sugars present in the molecule can be subjected, besides the etherification as methyl ethers, as already shown in the case of the α-L-thevetose, to an esterification with the above mentioned carboxylic acids, and preferably with the acetic acid, or, when pairs of hydroxy groups in the positions 1,2 or 1,3 having a proper steric orientation are involved, to an acetalization with an aldehyde or a ketone, preferably acetone.

More particularly, the following compounds are representative of those of the present invention: 3β, 14-dihydroxy-17 β-(4-pyridazinyl)-5β, 14β-androstane 3β-(-tris-β-D-digitoxopyranosyloxy)-14-hydroxy-17β-(4-pyridazinyl)-5β, 14β-androstane 3β-(tris-β-D-digitoxopyranosyloxy)-12β, 14-dihydroxy-17β-(4-pyridazinyl)-5β, 14β-androstane 3β-(4'''-0-methyl-tris-β-D-digitoxopyranosyloxy)-12β, 14-dihydroxy-17β-(4-pyridazinyl)-5β, 14β-androstane 3β, 5, 14, 19-tetrahydroxy-17β-(4-pyridazinyl)-5β, 14β-androstane 3β-(α-L-rhamnopyranosyloxy)-5, 14, 19-trihydroxy-17β-(4-pyridazinyl)-5β, 14β-androstane 3β-(α-L-3,4-0-isopropylidenrhamnopyranosyloxy)-5, 14, 19-trihydroxy-17β-(4-pyrodazinyl)-5β, 14β-androstane 3β-(α-L-thevetopyranosyloxy)-14-hydroxy-17β-(4-pyridazinyl)-5β, 14β-androstane 3β-(α-L-2,4-0-diacetylthevetopyranosyloxy)-14-hydroxy-17β-(4-pyridazinyl)-5β, 14β-androstane 3β-(α-L-2,4-0-diformylthevetopyranosyloxy)-14-hydroxy-17β-(4-pyridazinyl)-5β, 14β-androstane 3β-(α-L-2,4-0-bis-(diethylaminoacetyl)-thevetopyranosyloxy)-14-hydroxy-17β-(4-pyridazinyl)-5β, 14β-androstane.

An object of the present invention is also a process for the synthesis of the novel steroid compounds of formula (1), which process is characterized by the following sequence of steps, namely:

(a) conversion of a starting compound having the formula (2)

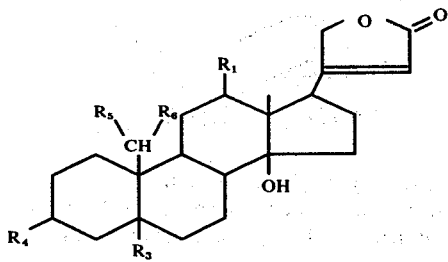

wherein $R_1$, $R_3$ and $R_4$ are as above identified, $R_5$ and $R_6$ represent two hydrogen atoms, or, if taken together, an oxygen atom, or even, when $R_5$ is an hydrogen atom, $R_6$ can take the meanings previously indicated with respect to $R_2$, and which represents a natural glycoside, particularly selected amongst those listed in L. Fieser and M. Fieser, loc. cit., or the corresponding genin, by reduction to the corresponding furyl derivative having the formula (3)

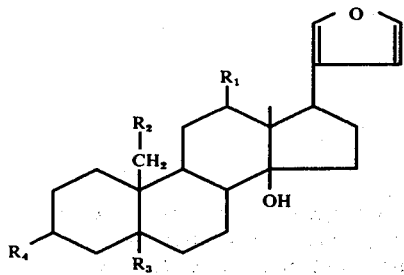

in which $R_2$ has the previously stated meaning; (b) conversion of the furyl derivative (3) to the 2-substituted maleic dialdehyde, either free or in the acetal form, having the formula (4)

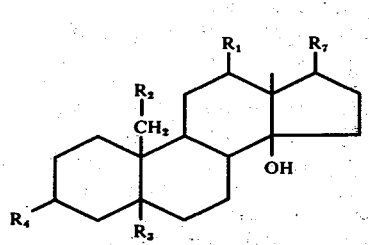

in which $R_7$ represents one of the following groups, corresponding to a 2-substituted maleic aldehyde, in free or acetal form:

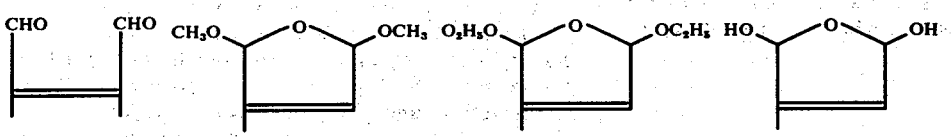

(c) reaction of the compound (4) with hydrazine at a temperature of between 20° and 150° C, thus obtaining the corresponding compound of formula (1).

Upon more detailedly considering the afore said steps of the process according to the present invention:
(1) the conversion of the compounds (2) to the furyl derivatives (3) can be carried out through a reduction, for instance through the reduction with diisobutylaluminium hydride according to the technique described from L. Minato and T. Nagasaki (Chem. and Industry, London, 1965,—pag. 899), suitably modified in account of the structure of the starting compound, in order to adjust this technique to the solubility and reactivity properties of the same starting compound. In this connection it is worthwhile to mention that, when in the molecule of the starting substance a free aldehydic group is present, as in the case of the strophanthidin and its derivatives, the latter is reduced from the diisobutylaluminium hydride to an alcoholic group;

(2) for the transformation of the compound (3) into the compound (4), when the compound (3) is the maleic dialdehyde, $R_7$ being

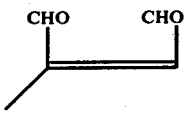

or into a corresponding hemiacetal or acetal derivative, of the type above referred to, use can be made of the known reactions for simple derivatives of the furane, such as the electrolytic oxidation or the oxidation with bromine in alcoholic solution according to N. Clausen-Kass (see, N. Elming, Advances in Organic Chemistry, 2 67 (1960)), or the addition according to Diels-Alder with diethyl azodicarboxylate (see, K. N. Zelenin, I. P. Bezhan, Zh. Organ. Khim., 2, 1529 (1966; Dodl. Akad. Nauk. USSR; 191, 1292 (1970)), possibly followed by an acid hydrolysis under mild conditions. It is however preferable, according to a feature of the present invention, that the conversion of the compounds of formula (3) to the compounds of formula (4) by reaction with an equivalent amount of a N-halo-amide or -imide, and particularly with N-bromo-succinimide at a temperature of between 2° and 20° C in the presence of weak bases or of buffers adapted to neutralize the hydrobromic acid formed in the reaction; particularly suitable is the sodium acetate. By having recourse to this technique, the maleic dialdehydes or their derivatives of formula (4) can be obtained, easily and with high yields, without modifications of the other functional groups present in the molecule and with a purity degree sufficient to permit their direct use in the subsequent step, without further treatment.

It is to be pointed out that, if the maleic dialdehyde is prepared in the free form, it could be also involved in an equilibrium with the form having an aldehyde group hemiacetalized with the hydroxy group present in the molecule in the 14β-position, as shown in the following formula:

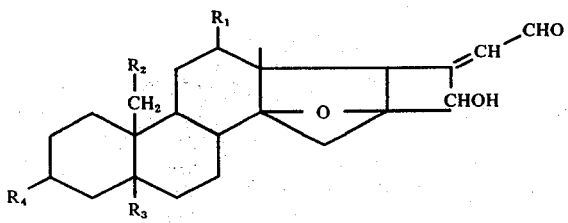

The existence of this form can be revealed by the nuclear magnetic resonance (NMR) spectra, recorded at 100 MHz, in dimethylsulphoxide solution: from the examination of these spectra the following bands are revealed (δ, ppm, tetramethylsilane as the internal standard)

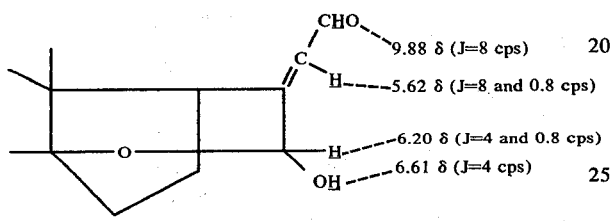

As already mentioned in the general definition of the compounds according to the present invention, some or all the hydroxy groups of the sugars present in the molecule can be etherified, esterified or even acetalized, and the presence of these groups can be desired in the final compound or their removal in the course or at the end of the synthesis can be necessary. Thus, apart from the preceding steps, the process according to the present invention can also be comprehensive of a further step, carried out according to the normal techniques of the organic chemistry, in order to introduce ether, ester or acetal groups which, as already explained, can be present in the steroid or in the glycoside moiety of the molecules of the compounds of the present invention.

This further step can be carried out either in advance of the steps of the above defined process according to the present invention, or can be interposed between any two steps of the same process, or even carried out after the last step of the present process; as already mentioned, the presence of these groups can be useful either in order to introduce these groups for modifying some features (adsorption, distribution in the tissues, etc.) of the pharmacological properties of the compounds of the present invention, or with the purpose of improving the synthesis process by varying the chemical characteristics (solubility, reactivity, etc.) of the intermediate compounds taking part into the synthesis.

In the latter case, the process can be comprehensive of a further step for the removal of the ether, ester or acetal groups as introduced in the intermediate compounds, when it is not desired to maintain these groups in the end product of the process; this further step also, effected according to the normal techniques of the organic chemistry, may be interposed between any two steps of the process of the invention or carried out at the end of the process. Sometimes, for such a further step, the same reagent used in a step of the process can be used, as for instance when an excess of hydrazine under suitable conditions is employed in the last step of the process, and therefore the simultaneous removal of one or more acetyl groups is achieved.

The compounds of the present invention are endowed with a relevant cardiokinetic activity, generally higher than that of the natural cardenolides of formula (2) and of the furane compounds of formula (3); they are moreover showing a moderate toxicity and have an improved therapeutical index with respect to that of the compounds of formula (2) and (3).

The following are two examples of clinical use which demonstrate the therapeutical efficiency of the compounds of the present invention:

(a) A patient (D. M. A., 61 years old, male), suffering from heart failure and from total respiratory insufficiency induced by obstructive chronic bronchopneumopathy was administered per os with a solution of 3β-(α-L-thevetopyranosyloxy)-14-hydroxy-17β-(4-pyridazinyl)-5β, 14β-androstane corresponding to the dosage of 0.33 mg. of the compound two times per day, for 26 days. The improvement was noticed immediately after the beginning of the treatment, the cardiac compensation being attained at the thirtheenth day; the compensation state was steadily maintained, even during tests of physical exercise, until the twenty-sixth day, when the patient was discharged from the hospital.

Figure 2:
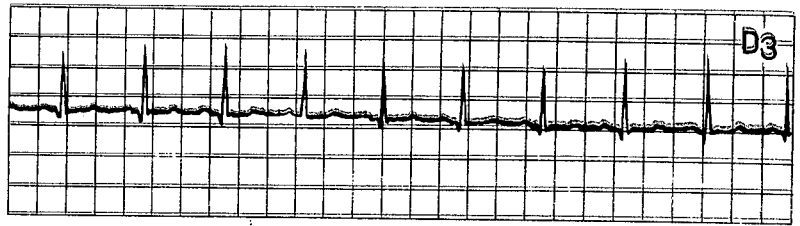

(b) A patient (S. G., 41 year old, male sex) was hospitalized for a supraventricular paroxysmal tachycardia, occurred in wellbeing conditions; the patient made record of a similar event occurred two years before. A vial containing a solution 0.5 mg. of 3β-(α-L-thevetopyranosyloxy)-14-hydroxy-17β-(4-pyridazinyl)-5β, 14β-androstane was administered intravenously. Before the injection an ECG was recorded, the $D_3$ lead of which is shown in the FIG. 1. After 10 minutes the heart rate frequency, as checked by auscultation, was lowered to 92–96 heart-beats per minute. After 30 minutes, the frequency was restored to the normal values; the ECG was recorded, the $D_3$ lead of which is shown in the FIG. 2.

The compounds of the present invention can be formulated together with suitable eccipients and in suitable preparations for the pharmaceutical administration, such as the solutions for oral or injectable use, tablets, capsules or pills or gelatin pearls for oral use, tablets for administration under the tongue, either alone or in combination with other substances which can usefully enhance or complete the cardiokinetic effect.

The following examples are illustrating the present invention, without having any limiting purpose.

EXAMPLE 1

A solution of 25 gram of 3β, 14-dihydroxy-17β-(3-furyl)-5β, 14β-androstane or of an equivalent amount of the corresponding 3β-0-acetyl derivative in 700 mls of dioxane and 280 mls of water containing 19 g. of sodium acetate trihydrate is added, under stirring over 10 minutes at 5°–8° C, with 12.8 g. of N-bromosuccinimide in 100 mls of dioxane; at the end of the addition, the mixture is kept for one hour at room temperature, and then most of the solvent is evaporated under reduced pressure, the residue is diluted with cold water and filtered; the thus obtained product is dissolved in 220 mls of methanol and 220 mls of hydrazine hydrate; the solution is heated to boiling for 20 minutes and then evaporated. The residue is taken up with diluted hydrochloric acid, filtered, and the solution is slightly alkalinized with ammonia. The thus obtained precipitate is filtered off and crystallized from ethyl acetate. 3β, 14-dihydroxy-17β-(4-pyridazinyl)-5β, 14β-androstane is thus obtained, having melting point of 210°–213° C, [α]$_D$ = −12° (c=0.5, methanol).

EXAMPLE 2

To a solution of 22 g. of 3β-(tris-β-D-digitoxopyranosyloxy)-14-hydroxy-17β-(3-furyl)-5β, 14β-androstane in 550 mls of dioxane and 220 mls of water containing 8.1 g. of sodium acetate trihydrate, a solution of 5.3 g. of N-bromosuccinimide in 70 mls of dioxane is added over 10 minutes at 5° C; at the end the mixture is kept standing for 1.5 hours at room temperature, evaporated under reduced pressure, and the residue is taken up with water and extracted with chloroform; the extract is evaporated, the residue is taken up with 200 mls of methanol and 200 mls of hydrazine and heated to reflux for 20 minutes. The mixture is evaporated under reduced pressure, the residue is taken up with alcohol and acidified with picric acid; the picrate of the product is thus obtained as a precipitate, which is dissolved in chloroform and subjected to chromatography on neutral alumina (activity IV); by eluating with a mixture of chloroform-methanol (95:5), the 3β-(tris-β-D-digitoxopyranosyloxy)-14-hydroxy-17β-(4-pyridazinyl)-5β, 14β-androstane is obtained, m.p. 237°–239° C (from acetate), [α]$_D$ = + 2.7° (c=0.5, methanol).

EXAMPLE 3

A solution of 8.2 g. of 12,3′,3″,3‴, 4‴-0-pentaacetyl-3β-(tris-β-D-digitoxopyranosyloxy)-12β, 14-dihydroxy-17β-(3-furyl)-5β, 14β-androstane in 200 mls of dioxane and 85 mls of water containing 2.4 g. of sodium acetate trihydrate is supplemented under stirring at 5°–8° C over 10 minutes with 1.5 g. of N-bromosuccinimide in 25 mls of dioxane; the mixture is kept standing for one hour at room temperature, evaporated under reduced pressure, diluted with water and extracted with chloroform; the extract is evaporated and the residue is taken up with 85 mls of methanol and 70 mls of hydrazine hydrate. The mixture is heated to reflux for 20 minutes, evaporated and the thus obtained product is purified according to the technique described in the Example 2. The 3β-(tris-β-D-digitoxopyranosyloxy)-12β, 14-dihydroxy-17β-(4-pyridazinyl)-5β, 14β-androstane is thus obtained, having melting point of 221°–224° C, [α]$_D$ = + 3.7° (c=0.5, methanol).

EXAMPLE 4

A solution of 6 g. of 3β, 5, 14, 19-tetrahydroxy-17β-(3-furyl)-5β, 14β-androstane in 150 mls of dioxane and 60 mls of water containing 4.2 g. of sodium acetate trihydrate is supplemented over 10 minutes under stirring at 5°–8° C with 2.75 g. of N-bromosuccinimide in 30 mls of dioxane; the mixture is kept standing for one hour at room temperature, and evaporated under reduced pressure, then taken up with water and extracted with chloroform. The chloroform extract is evaporated, the residue is taken up with 50 mls of methanol and 50 mls of hydrazine hydrate. The mixture is heated to reflux for 20 minutes. Upon evaporation under reduced pressure, the residue is crushed with ether and filtered. The product is purified through chromatography on neutral alumina (activity IV), by eluting with a mixture of chloroform-methanol (95:5). The 3β, 5, 14, 19-tetrahydroxy-17β-(4-pyridazinyl)-5β, 14β-androstane is thus obtained, m.p. 142°–145° C (from methanol); picrate, m.p. 138°–140° C.

EXAMPLE 5

A solution of 5 g. of 3β-(α-L-3,4-0-isopropylidenrhamnopyranosyloxy)-5, 15, 19-trihydroxy-17β-(3-furyl)-5β, 14β-androstane in 125 mls of dioxane and 50 mls of water containing 2.35 g. of sodium acetate trihydrate is supplemented, under stirring at 5°–8° C over 10 minutes, with 1.55 g. of N-bromosuccinimide in 20 mls of dioxane. The mixture is kept standing for one hour at room temperature, and evaporated under reduced pressure, the residue being then taken up with water, extracted with chloroform and evaporated; the residue is taken up with 35 mls of methanol and 35 mls of hydrazine hydrate; the mixture is boiled to reflux for 20 minutes, and evaporated under reduced pressure; the residue is crushed with ether and filtered. The product is purified by chromatography on silica gel, a mixture of ethyl acetate-methanol (98:2) being used as the eluent. The 3β-(α-L-3,4-0-isopropylidenrhamnopyranosyloxy)-5, 14, 19-trihydroxy-17β-(4-pyridazinyl)-5β, 14β-androstane is thus obtained, m.p. 257°–259° C, [α]$_D$ = −7.6° (c=0.5, methanol).

In order to prepare the 3β-(α-L-rhamnopyranosyloxy)-5, 14, 19-trihydroxy-17β-(4-pyridazinyl)-5β, 14β-androstane, the afore said isopropyliden derivative is hydrolized in methanol solution with N hydrochloric acid at room temperature for 3 hours; the thus obtained product has a melting point of 223°–225° C.

EXAMPLE 6

A solution of 10 g. of 3β-(α-L-thevetopyranosyloxy)-14-hydroxy-17β-(3-furyl)-5β, 14β-androstane in 250 mls of dioxane and 100 mls of water containing 5.5 g. of sodium acetate trihydrate is supplemented, over 10 minutes under stirring at 5°–8° C, with 3.45 g. of N-bromosuccinimide in 40 mls of dioxane; the mixture is kept standing for one hour at room temperature, evaporated under reduced pressure, taken up with water and extracted with chloroform. The extract is evaporated and the residue is taken up with 100 mls of methanol and 100 mls of hydrazine hydrate. The mixture is boiled to reflux for 30 minutes, evaporated under reduced pressure, the residue is taken up with diluted hydrochloric acid and the solution is washed with ether. The acid solution is made alkaline with ammonia and the thus precipitated product is purified by chrommatography on neutral alumina (activity IV), chloroform-methanol (95:5) being used as the eluent. The 3β-(α-L-thevetopyranosyloxy)-14-hydroxy-17β-(4-pyridazinyl)-5β, 14β-androstane is thus obtained, m.p. 258°–260° C, [α]$_D$ = −74° (c=1, methanol). By acetilating this compound with acetic anhydride in pyridine at room temperature for 36 hours, the 3β-(α-L-2,4-0-diacetylthevetopyranosyloxy)-14-hydroxy-17β-(4-pyridazinyl)-5β, 14β-androstane is obtained, m.p. 177°–178° C (from ethyl acetate), [α]$_D$ = −94.5° (c= 1, methanol).

EXAMPLE 7

A solution of 1 g. of 3β-(α-L-thevetopyranosyloxy)-14-hydroxy-17β-(4-pyridazinyl)-5β, 14β-androstane in 250 mls of alcohol is supplemented with 250 mls of glycerine. The mixture is diluted to one liter of water. The 1% solution thus prepared is partitioned in bottles of suitable capacity and provided with eye droppers for the oral administration.

EXAMPLE 8

An alcoholic solution of 2.5 g. of 3β-(α-L-thevetopyranosyloxy)-14-hydroxy-17β-(4-pyridazinyl)-5β, 14β-androstane in one liter of alcohol is supplemented with 1,250 mls of glycerine; the mixture is diluted to 10 liters with bidistilled water and the solution is partitioned in vials, each containing 2 mls of the solution, the vials being then welded and sterilized at 115° C for 30 minutes. The thus prepared vials are adapted for the intravenous or intermuscular administration.

EXAMPLE 9

By respectively repeating the Examples 7 and 8, except that an equal amount of 3β-(tris-β-D-digitoxopyranosyloxy)-12β, 14-hydroxy-17β-(4-pyridazinyl)-5β, 14β-androstane is substituted for the 3β-(α-L-thevetopyranosyloxy)-14-hydroxy-17β-(4-pyridazinyl)-5β, 14β-androstane, preparations are obtained of the former substance which are respectively suitable for the oral and the intravenous/intermuscular administration.

What we claim is:

1. Novel cardiotonic steroid compounds and their glycoside derivatives containing a pyridazine ring, having the formula (1)

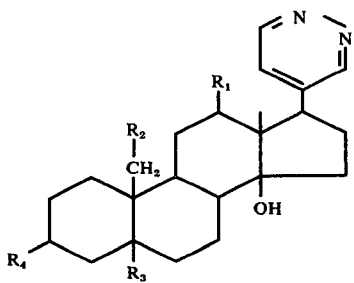

in which $R_1$ and $R_2$ are hydrogen or a hydroxy group, either free or esterified with a carboxylic aliphatic acid selected from the group consisting of formic acid, acetic acid, propionic acid and butyric acid, $R_3$ is hydrogen or a hydroxy group and $R_4$ is a hydroxy group or a hexopyranoside unit or a chain of two or three hexopyranoside units, some or all of the hydroxy groups contained in the $R_4$ substituent being either free or etherified as the methyl ether, or esterified with formic acid, acetic acid, propionic acid or butyric acid or bearing basic groups, or when $R_4$ is a hexopyranoside unit or a chain of two or three hexopyranoside units having a pair of hydroxy groups in the positions 1, 2 or 1, 3 the acetal with acetone.

2. A compound according to claim 1, which is 3β, 14-dihydroxy-17β-(4-pyridazinyl)-5β, 14β-androstane.

3. A compound according to claim 1, which is 3β-(tris-β-D-digitoxopyranosyloxy)-14-hydroxy-17β-(4-pyridazinyl)-5β, 14β-androstane.

4. A compound according to claim 1, which is 3β-(tris-β-D-digitoxopyranosyloxy)-12β, 14-dihydroxy-17β-(4-pyridazinyl)-5β, 14β-androstane.

5. A compound according to claim 1, which is 3β-(4'''-O-methyl-tris-β-O-digitoxopyranosyloxy)-12β, 14-dihydroxy-17β-(4-pyridazinyl)-5β, 14β-androstane.

6. A compound according to claim 1, which is 3β, 5, 14, 19-tetrahydroxy-17β-(4-pyridazinyl)-5β, 14β-androstane.

7. A compound according to claim 1, which is 3β-(α-L-rhamnopyranosyloxy)-5, 14, 19-trihydroxy-17β-(4-pyridazinyl)-5β, 14β-androstane.

8. A compound according to claim 1, which is 3β-(α-L-3,4-O-isopropylidenrhamnopyranosyloxy)-5, 14, 19-trihydroxy-17β-(4-pyridazinyl)-5β, 14β-androstane.

9. A compound according to claim 1, which is 3β-(α-L-thevetopyranosyloxy)-14-hydroxy-17β-(4-pyridazinyl)-5β, 14β-androstane.

10. A compound according to claim 1, which is 3β-(α-L-2,4-O-diacetylthevetopyranosyloxy)-14-hydroxy-17β-(4-pyridazinyl)-5β, 14β-androstane.

11. A compound according to claim 1, which is 3β-(α-L-2,4-O-diformylthevetopyranosyloxy)-14-hydroxy-17β-(4-pyridazinyl)-5β, 14β-androstane.

12. A compound according to claim 1, which is 3β-(α-L-2,4-O-bis-(diethylaminoacetyl)-thevetopyranosyloxy)-14-hydroxy-17β-(4-pyridazinyl)-5β, 14β-androstane.

13. A process for the synthesis of the steroid compounds according to claim 1 comprising converting the furyl containing compound of formula (2)

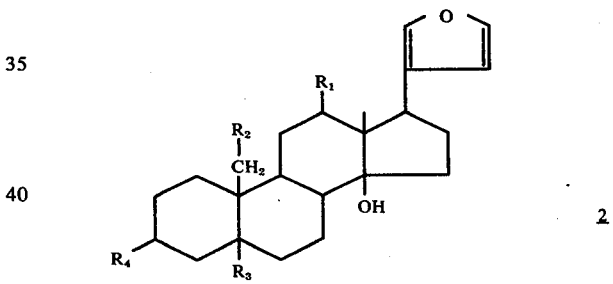

into the 2-substituted maleic dialdehyde, of formula (3), either in free form or acetalyzed,

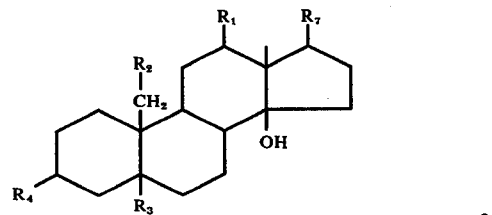

wherein $R_7$ represents one of the following groups:

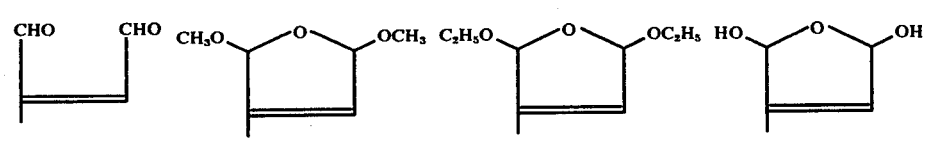

into the reaction of the compound (3) with hydrazine at a temperature of between 20° and 150° C, thus obtaining the corresponding compound of formula (1), said conversion being carried out by (a) electrolytical oxidation, (b) oxidation with bromine in alcoholic solution, (c) addition according to Diels-Alder of diethyl azodicarboxylate with subsequent acid hydrolysis under mild conditions, or (d) reaction with a N-halo-amide or -imide in the presence of an acceptor for hydrogen halide which is a weak base or buffer.

14. A process according to claim 13, characterized in that the conversion of the compound of formula (3) into that of formula (4) takes place through oxidation, either electrolytically or with bromine in alcoholic solution, followed by an acid hydrolysis under mild conditions.

15. A process according to claim 13, characterized in that the conversion of the compound of formula (3) into that of formula (4) takes place by addition according to Diels-Alder of diethyl-azodicarboxylate, and subsequent acid hydrolysis under mild conditions.

16. A process according to claim 13, characterized in that the conversion of the compound of formula (3) into that of formula (4) takes place by reaction with a N-halo-amide or -imide in the presence of an acceptor hydrogen halide, selected amongst weak bases and the buffer compounds.

17. A process according to claim 16, characterized in that as the N-halo-imide, N-bromo-succinimide is used, and as the hydrogen halide acceptor, sodium acetate is used.

18. A pharmaceutical composition having cardiotonic effect, characterized in that it contains, as the active ingredients, a compound according to the claim 1.

* * * * *